United States Patent [19]

Teague, Jr. et al.

[11] 4,210,975

[45] Jul. 8, 1980

[54] FLUID LINE AND CONNECTION FOR FLUID-DRIVEN APPLIANCE

[76] Inventors: Walter D. Teague, Jr., Tweed Blvd., Nyack, N.Y. 10960; Arthur T. Sempliner, 37-04 Van Nostrand Pl., Douglaston, Nebr.W YORK 11363

[21] Appl. No.: 920,685

[22] Filed: Jun. 30, 1978

[51] Int. Cl.[2] .............................................. A46B 13/02
[52] U.S. Cl. .................................... 15/22 R; 173/168; 285/134; 433/133
[58] Field of Search ...................... 15/22 R, 24, 29, 23, 15/28; 32/27; 285/134; 137/562; 128/47, 50, 53, 56, 62 A; 173/168, 169; 51/134.5 F, 170 MT

[56] References Cited

U.S. PATENT DOCUMENTS

| | | | |
|---|---|---|---|
| 2,834,465 | 5/1958 | McMichael | 285/134 X |
| 3,046,585 | 7/1962 | Ledingham et al. | 15/24 |
| 3,502,158 | 3/1970 | Snider | 173/169 X |
| 4,090,539 | 5/1978 | Krupp | 285/134 X |

Primary Examiner—Edward L. Roberts
Attorney, Agent, or Firm—Mandeville and Schweitzer

[57] ABSTRACT

The disclosure is directed to a flexible fluid line arrangement suited for connecting a hand held fluid-driven appliance to a source of motive fluid in a manner providing reliable, effective fluid supply, while permitting easy and facile manual manipulation of the appliance. The application specifically discloses a water driven power toothbrush adapted for connection to a household faucet. Concentrically arranged tubes connect the faucet with the hand held appliance, with the pressure side of the faucet connected to the innermost tube, while the exhaust or discharge side connects to the annular space between the inner and outer tubes. Novel, simplified swivel connections are provided between the appliance and the concentric tubes, and also between the tubes and the outlet fitting at the faucet.

12 Claims, 5 Drawing Figures

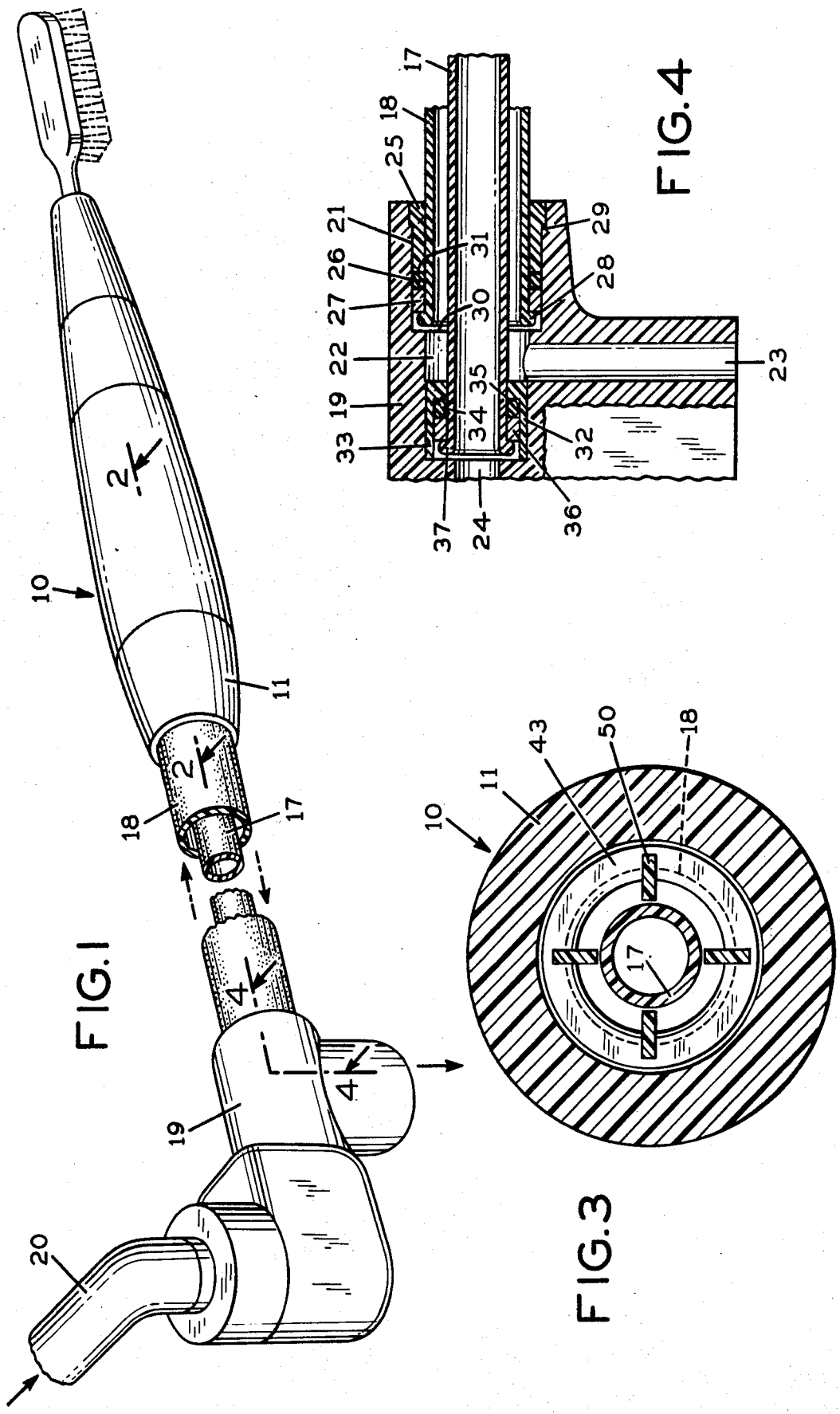

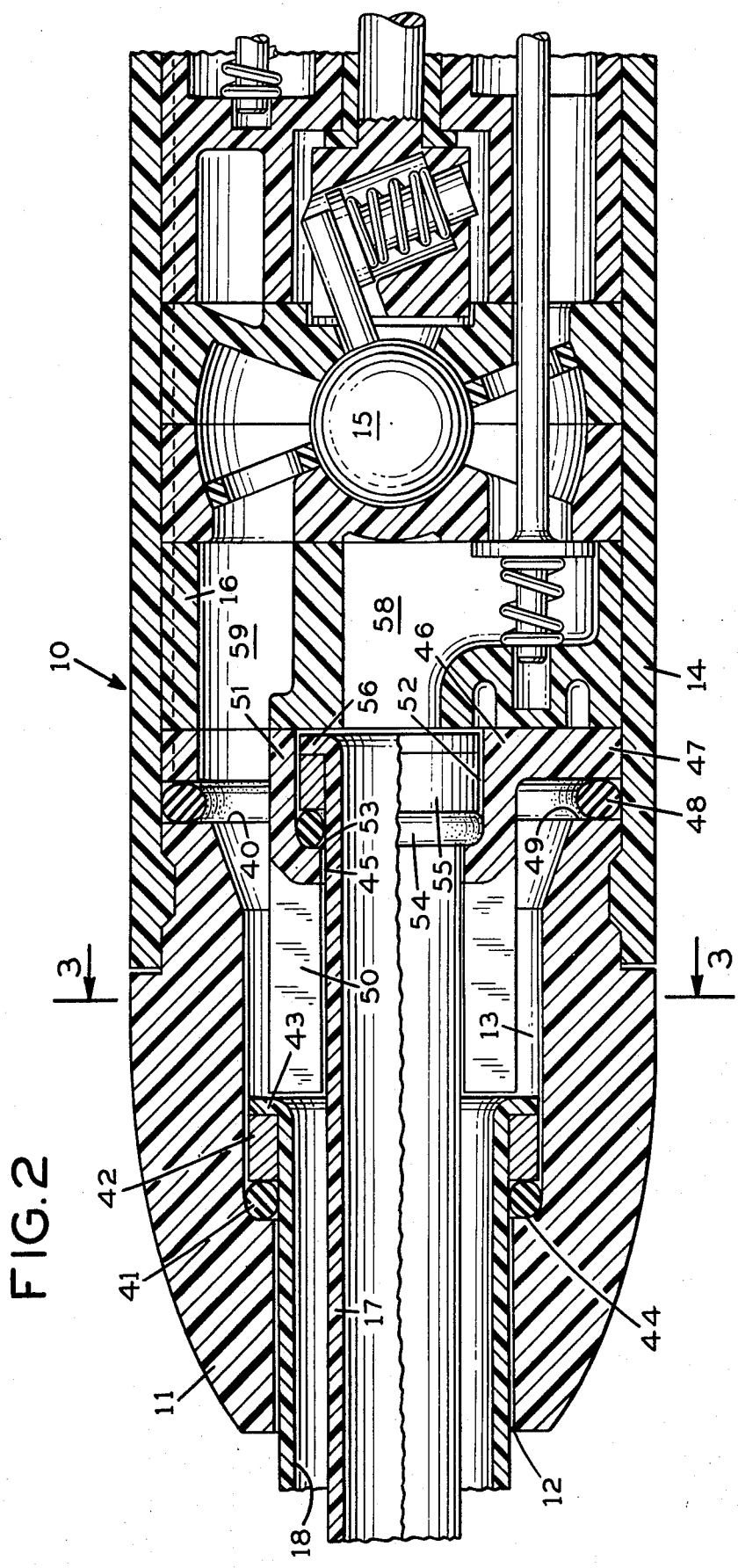

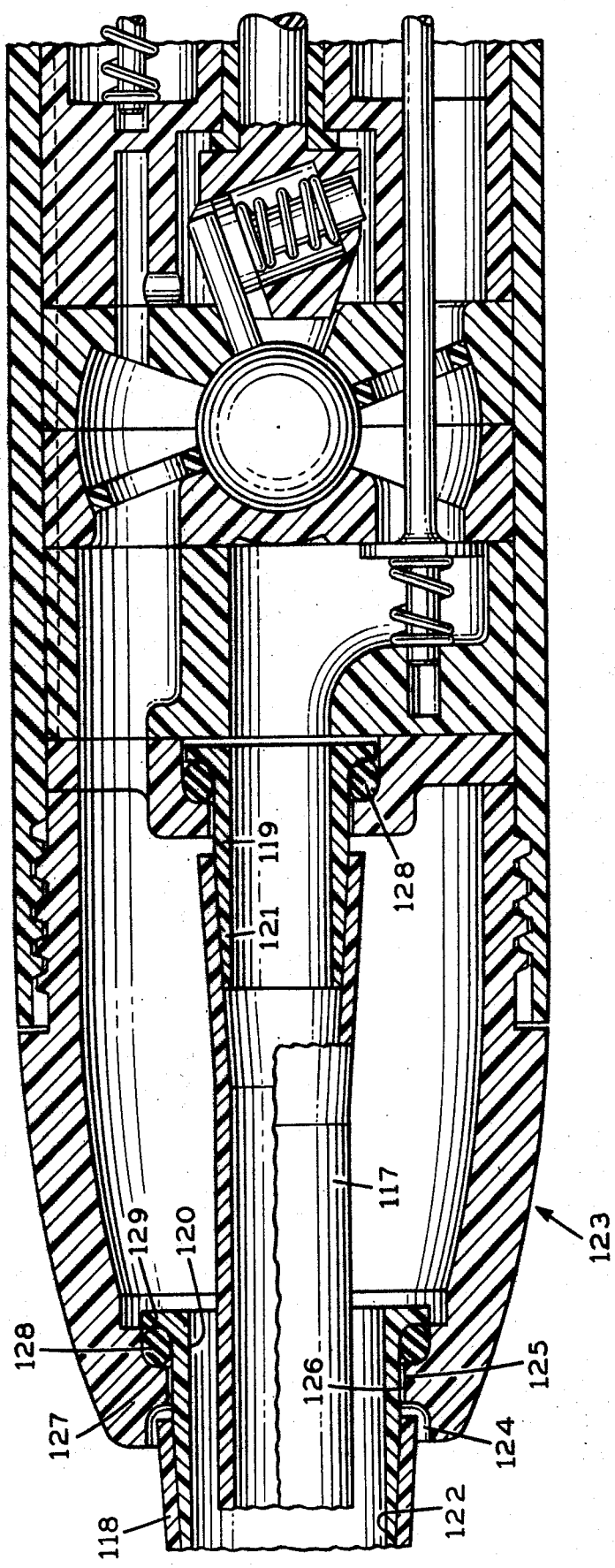

FLUID LINE AND CONNECTION FOR FLUID-DRIVEN APPLIANCE

BACKGROUND AND SUMMARY OF THE INVENTION

The present invention is intended particularly for, although not necessarily limited to, utilization in connection with a small, hand held, fluid-driven appliance, such as a power toothbrush. Electrically driven power toothbrushes are well known and widely utilized. Recently, improvements in the design and construction of fluid motors has made it possible to incorporate a water driven motor into the base of a hand held toothbrush appliance, in a manner to provide a brushing device having superior functional and other characteristics. Certain aspects of such a device are disclosed and claimed in our earlier United States patent application Ser. No. 848,807, filed Nov. 7, 1977 now U.S. Pat. No. 4,175,299.

In the operation of a water driven appliance, such as a toothbrush, provision must be made for easy movement of the appliance in a universal manner, to accommodate all of the various natural motions and orientations involved in brushing all of the surfaces of the teeth and gums. At the same time, provision must be made for containing a rather substantial fluid pressure, at least on the high pressure side of the fluid connection. These two requirements, of course, tend to be somewhat contradictory. However, the arrangement of the invention provides for a highly optimized solution to the problems.

In accordance with the invention, a bidirectional fluid hose connection, between a fluid source and a hand held appliance, is provided in the form of a dual concentric tube arrangement, with each tube being provided with a highly simplified yet effective swivel connection at each end to accommodate relative rotation of the appliance without twisting and kinking the tubing. The inner tubing element, according to the invention, is constructed of a flexible, plastic material suitable to withstand the inlet-side pressure to which the device will be exposed. The larger, outer tubing element is likewise constructed of a flexible plastic material, but since it is connected to exhaust, it need not be designed to withstand significant pressure. Since the inner, high pressure element is of relatively small diameter, wall stresses per unit of pressure are minimized. Moreover, since the high pressure element is wholly concealed within the larger outer element, the materials utilized in the high pressure tubing may be selected exclusively on the basis of functional considerations and without regard to cosmetic aspects. The outer tubing, on the other hand, may be selected primarily to satisfy cosmetic considerations, since the functional requirements imposed on it are relatively minimal. The concentric hose construction not only facilitates easy relative rotation of the hand held appliance, but also accommodates neat and easy coiling the tubing for storage of the appliance after use.

In accordance with one of the specific aspects of the invention, simplified and economical, yet highly effective arrangements are provided for engaging the concentric tubing elements in operative relation with both the hand held appliance and a faucet attachment fitting, in a manner providing for relative rotational movement of the tubing, appliance and fitting. The arrangement of the invention enables a swivel connection to be provided without adding significantly to the physical bulk or weight of the elements, both important considerations in the design of a hand held appliance, such as a power toothbrush.

For a more complete understanding of the above and other features and advantages of the invention, reference should be made to the following detailed description of preferred embodiments and to the accompanying drawings.

DESCRIPTION OF THE DRAWINGS

FIG. 1 is a perspective view of a hand held, fluid-driven toothbrush appliance utilizing a concentric tube fluid connection incorporating features of the invention.

FIG. 2 is an enlarged, fragmentary cross sectional view through the base of the appliance, as taken generally on line 2—2 of FIG. 1.

FIG. 3 is a cross sectional view taken generally on line 3—3 of FIG. 2.

FIG. 4 is a fragmentary cross sectional view as taken generally on line 4—4 of FIG. 1.

FIG. 5 is an enlarged cross sectional view, similar to FIG. 2, illustrating a modified form of swivel connection for the concentric tube arrangement.

DESCRIPTION OF PREFERRED EMBODIMENTS OF THE INVENTION

Referring now to the drawings, and initially to FIGS. 1-4 thereof, the reference numeral 10 designates generally the body of a hand held, fluid-driven appliance, such as a power toothbrush. It will be understood, however, while the invention is useful to great advantage in connection with a fluid-driven toothbrush, a variety of appliances may be utilized in conjunction with the invention. Likewise, the details of form and operation of the appliance are not critical to either the invention or an understanding thereof.

With reference now particularly to FIG. 2, there is shown a fragmentary portion of the main housing of a power driven toothbrush. In a typical embodiment, the housing 10 may have a diameter on the order of 2.5-3 cm. The housing 10 includes a base cap member 11, typically of molded plastic, which has an entrance passage 12 at one end and an enlarged cavity 13 communicating with the passage 12. The base cap 11 may be threadedly or otherwise secured to a tubular main housing section 14. In the illustrated arrangement, a fluid-driven, nutating motor assembly, generally designated by the numeral 15, is mounted and contained within the housing sleeve 14, being held in position by a spacing collar 16.

Pursuant to one aspect of the invention, a pair of concentrically arranged, flexible tubes 17, 18 are received in the passage 12 and communicate with the interior of the appliance housing 10, in a manner to be further described. As reflected in FIG. 1, the concentric tubes 17, 18 extend from the appliance for an appropriate distance, suitable to the intended utilization, and are connected at their upstream ends to a fitting 19, sometimes referred to as a diverter, which is removably attached to a fluid supply conduit 20, typically a household faucet.

With reference to FIG. 4, the diverter fitting 19 includes a large diameter outlet passage 21, into which extend both of the concentrically arranged tubes 17, 18. The larger diameter, outer tube 18 terminates in communication with an exhaust chamber 22 which in turn is in communication with a discharge outlet 23. The innermost tube 17 extends through the discharge chamber 22 and communicates with a supply passage 24. The passage 24 is connected, through the body of the diverter fitting 19 to the faucet 20.

Pursuant to one aspect of the invention, a simplified, economical yet effective swivel fluid connection is provided for connecting each of the concentric tubes 17, 18 to the diverter fitting 19 (and/or to the appliance). To this end, the tubes advantageously are formed of a flexible, thermoplastic material, such as vinyl. In a preparatory procedure, a cylindrical plastic sleeve 25 is slipped over the upstream end of the outer tube 18, followed by an O-ring 26 and a metal collar 27. Following this preassembly, the tubing end is thermoplastically deformed to provide an outwardly extending integral flange 28.

To assembly the outer tube with the diverter fitting 19, the preassembly of the tube 18, collar 27, O-ring 26 and sleeve 25 are inserted in the large diameter outlet opening 21 in the diverter fitting. To advantage, the sleeve 25 is provided with a shoulder 29 which seats against a corresponding shoulder within the fitting 19, to position the sleeve. The sleeve may be permanently secured by adhesive bonding, or may be removably secured by threads, as desired. The sizing of the O-ring 26 and tubing 18, in conjunction with the inlet passage 21, is such that the O-ring lightly contacts the wall of the tubing to form a seal.

As shown in FIG. 4, a shoulder 30 is formed where the main inlet passage 21 meets the somewhat smaller diameter exhaust chamber 22. The spacing between the shoulder 30 and the end face 31 of the plastic sleeve 25 is such as to provide a slight axial clearance between a tubing flange 28 and the shoulder 30, with the O-ring 26 and metal collar 27 in their properly assembled positions. This permits relative rotation to occur between the outer tube 18 and the fitting 19, while at the same time providing for an effective seal by the O-ring 26.

A somewhat similar arrangement is provided for connecting the inside tubing element 17 to the fitting, it being understood, of course, that in a normal assembly procedure, the inside tube 17 would be connected to the fitting before the outside tube 18. For the inside tube, there is provided an internally shouldered plastic sleeve 32, which is received over the O.D. of the inside tube 17 and is slideably received within an extension 33 of the recess which forms the exhaust chamber 22. An O-ring 34 is applied over the tube 17 and seated against the internal shoulder 35 of the plastic sleeve. A metal collar 36 is applied over the tube and serves to confine the O-ring 34, in combination with the shoulder 35.

After initial preassembly of the sleeve 32, O-ring 34 and collar 36, the tubing 17 is thermoplastically deformed to provide a flange 37 overlying the end of the metal collar 36. As illustrated in FIG. 4, the length of the plastic sleeve 32, is such as to provide a slight clearance beyond the end of the flange 37, to accommodate relative rotation of the inside tube 17 as necessary. As in the case of the outer tube 18, the O-ring 34 lightly contacts the O.D. of the tube 17 and the I.D. of the plastic sleeve 32 to provide an effective fluid seal. The sleeve 32 may be cemented or otherwise secured in its assembled position.

Referring now to FIG. 2, the downstream or discharge end of the concentric tubing assembly 17, 18 is rotatably connected to the appliance housing 10 in a manner generally similar to its connections to the diverter fitting 19. More specifically, the concentrically arranged tubes are inserted through the entrance passage 12 until they are accessible beyond the open end 40 of the base cap 11. An O-ring 41 and metal collar 42 are received over the O.D. of the outer tube 18, and the end extremity of the tube is then thermoplastically shaped to form a flange 43 overlying the metal ring. The outer tube is then drawn down into the cap recess 13, until the O-ring 41 seats against an internal shoulder 44 in the base cap. The O-ring is sized to lightly engage the outer wall of the tube 18 and the inner wall of the recess 13 to form a seal, while permitting rotation of the tube 18 relative to the cap 11. Typically, a slight annular clearance is provided around the outside of the ring 42, as illustrated in FIG. 2, and this would also be the case with respect to the collars 27, 36 at the diverter end.

As reflected in FIG. 2, the inside tube 17 extends somewhat beyond the end of the outer tube 18 and is received through a central opening 45 in a divider element 46. The divider element 46 is formed with an outwardly extending flange 47, which is seated on one face against the spacer element 16. On the other face, the flange 47 is seated against an O-ring 48, which is compressed between the flange 47 and the annular end face 49 of the cap 11. The divider element 46 has a plurality of axially extending, angularly spaced legs 50, which extend from the base of the spacer in a direction toward the end flange 43 of the outer tube 18. The spacer legs 50 serve to confine generally the flange 43 to the assembled position illustrated in FIG. 2, while providing a slight clearance.

At the base end of the spacer 46 there is formed a central cup 51 having an internal recess 52 and a forwardly facing shoulder 53. Received within the recess 52 are an O-ring 54 and a metal collar 55. These are applied over the O.D. of the inside tube 17, after which the tube is deformed to provide a flange 56 overlying the outer end of the collar 55. The cup 51 seats against passage forming walls 57 of the spacer element 16, serving to confine the flanged end of the inside tube 17 within the cup recess 52 while providing sufficient clearance to accommodate relative rotary motion.

In the assembled structure illustrated in FIG. 2, the inside tube 17 communicates with an inlet passage 58, leading to the inlet of the fluid motor 15. An outlet passage 59, also formed in the spacer element 16, communicates with the large chamber 13 in the end cap 11, and this in turn is open to the annular end opening formed by the outer tube 18 surrounding the inside tube 17.

In the structure thus illustrated in FIGS. 1–4, water under pressure discharged from the faucet 20 enters the diverter fitting 19 and flows into the inside flexible tube 17 through a first rotary seal. At the appliance end, the fluid under pressure is discharged from the tube 17 into the inlet passage 58 and eventually passes through the fluid motor 15. The exhaust fluid passes into the chamber 13, flows through the annular passage surrounding the tube 17, and is discharged to exhaust at the diverter fitting end. In a typical practical embodiment of the invention, the inside tube 17 may have an I.D. on the order of about 5 mm, and the outer tube 18 may have a I.D. of around 12 mm, for example. Significant practical advantages are realized by arranging the pressure or inlet tube to be inside the exhaust fluid tube. In part, important advantages are derived from the fact that the pressure tube may be thus relatively small in diameter, minimizing wall stress for a given amount of pressure and thus enabling the tubing to have relatively greater flexibility and ease of coiling. Moreover, because the inside tube is totally concealed, it may be formed of a material selected exclusively for its physical characteristics and without regard to its appearance. When the appliance is being operated, moreover, there is at least a slight back pressure within the annular exhaust passage surrounding the inside tube 17, and this tends partially to balance the higher pressure of the incoming fluid.

While the inside tube 17 may be designed exclusively with reference to its physical characteristics, the outside tube 18 may largely be designed with primary reference to appearance characteristics. Since the outer tube carries an absolute minimum of pressure at any time, being open to exhaust at the diverter end, the outer tube need not have significant strength. However, since cosmetic considerations can be quite significant to the successful marketing of an appliance such as a power toothbrush, the ability to select a tubing material primarily for its attractive appearance represents a significant practical advantage.

The simple swivel connection arrangment enables relatively free rotation of the appliance relative to the connecting tubes, and also the tubes relative to the diverter fitting. The form of the rotary connection is extremely simplified and economical, but adequate for the purpose. Perhaps more importantly, the rotary connection is accomplished with components of a diameter not greatly exceeding that of the tubing itself. This is of particular significance with respect to an appliance such as a hand held toothbrush, for example, where overall bulk and weight are significant factors.

In FIG. 5 of the drawing, there is shown an advantageous modification of the rotary seal arrangement, which is adapted to provide a highly effective seal without relying upon the specific physical characteristics of the tubing for this purpose. In the modification of FIG. 5, each of the inside and outside tubes 117, 118 is provided at its end extremities with a flanged connector fitting 119, 120. The flanged connector fittings are arranged to be received tightly within the ends of the flexible tubes 117, 118, and may be provided with tapered end wall areas 121, 122 to facilitate assembly. The end fittings may be secured to the tubes by friction or adhesive bonding.

The flanged end fittings 119, 120 advantageously are of molded plastic construction, of a material somewhat more rigid than that of the flexible tubes 117, 118.

In the embodiment of FIG. 5, the base cap 123 is provided at its lower end with an enlarged recess 124 adjacent the outer end of the passage 125 through which the flanged fitting 120 extends. The end extremity of the tubing 118, where it is secured to the flanged fitting, is received within the recess 124 and thus concealed from view. In addition, the clearance space 126, between the wall of the flanged fitting 120 and the passage 125, is substantially narrower than the wall thickness of the tubing 118, such that the tubing itself cannot enter the passage 125.

At the inside end of the passage 125, there is a recess 127, in which is seated an O-ring 128. The flange 129 of the fitting 120 is seated on the opposite side of the O-ring. As is evident in FIG. 5, the end extremity of the tubing 118, being positioned closely adjacent to the bottom of the recess 124, serves to limit any inward movement of the fitting 120, eliminating the need for means such as the spaced legs 50, in the embodiment of FIGS. 1-4.

The embodiment of FIG. 5 is particularly advantageous where large production volumes are required and/or where relatively high operating pressures are involved. By providing a precision molded, standardized connector fitting, greater dimensional consistency is possible than when utilizing the tubing itself to form the flanged seal and to cooperate with the O-ring. In this respect, standard, commercially available tubing is not generally produced to dimensional tolerances which are as tight as may be desirable. Likewise, by utilizing a precision molded, standardized flanged swivel fitting, it is possible to select tubing which is somewhat more soft and flexible than where the properties of the tubing itself are relied upon for purposes of retaining the tubing in position by means of an integral flange.

It should be understood, of course, that the modified form of swivel connection, shown in FIG. 5 in association with a hand held appliance, would also be useable at the diverter end of the concentric tube arrangement.

The invention provides a novel and improved fluid supply system, which is particularly useful in connection with a fluid-driven, hand held appliance. Particularly where the hand held appliance must be small, lightweight and highly manipulatable, as in the case of a power driven toothbrush, it is extremely desirable to provide for a swivel or rotary connection between the appliance and the fluid source. By providing inlet and outlet tubes in concentric arrangement, it is possible to incorporate swivel connections of a simplified and inexpensive nature, and which, pursuant to one of the more specific aspects of the invention, do not add significantly to the weight or bulk or manufacturing cost of the device.

Unique advantages are derived, for the intended end use, by arrangement of the concentric tubes with the pressure tube contained within the exhaust tube. The pressure tube thus may be formed of material selected exclusively for physical properties and without regard to appearance. The smaller diameter of the pressure tube also enables its wall thickness to be smaller, for optimum flexibility. The necessarily larger diameter outer tube, being required to contain only the exhaust fluid at minimum pressure, may be formed of a material selected almost exclusively for appearance characteristics, in terms of being able to be produced in desirable colors, etc.

Important advantages are also derived from the use of a highly simplified, easily assembled and compact swivel connection arrangement, which utilizes a simple O-ring seal in conjunction with a flanged end of the tubing or a separate, flanged fitting. In either form, the swivel connection is easily and inexpensively assembled and is highly effective for the purposes intended.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

We claim:

1. In the combination of a fluid device and a fluid conduit means connected to said device, said conduit means including first and second flexible tubes arranged concentrically, a swivel connection means for connecting said conduit means to said device, characterized by (a) each of said flexible tubes including open end forming means,
(b) passage means in said device for receiving the end forming means of said first and second flexible tubes,
(c) O-ring elements associated with the end forming means of each of said tubes,
(d) internal shoulders formed within said passage means and forming seats for said O-ring elements,
(e) each of said O-ring elements being seated against one of said seats to retain said tubes in said passage means and being in a light, sealing relation with the complementary internal shoulder, the passage means, and the end forming means of the complementary flexible tube, whereby said O-ring elements form a seal around their respective tubes while permitting rotation of each of the tubes relative to the passage means of said device, and
(f) flange means extending radially outward from the end forming means of each of said tubes and overlying said O-ring elements on the sides thereof opposite said internal shoulders.

2. The combination of claim 1, further characterized by
(a) said fluid device comprising a hand-held fluid-powered appliance.

3. The combination of claim 2, further characterized by
(a) said first tube being received within said second tube,
(b) said appliance having a base cap member,
(c) said passage means including an entrance passage formed in said base cap member for communicating with said second, outer tube,
(d) a flanged, sleeve-like element extending through said entrance passage and received within said second tube,
(e) said base cap member having an external recess surrounding said entrance passage and receiving the end extremity of said second tube.

4. The combination of claim 3, further characterized by
(a) one of said internal shoulders comprising an internal recess formed in said base cap member, and
(b) one of said O-ring elements being seated in said internal recess and engaging said sleeve-like element.

5. The combination of claim 5, further characterized by (a) said passage means including a circular opening for the reception of the end forming means of the first inner tube, and
(b) said flange means being located at one end and being of larger diameter than said circular opening.

6. The combination of claim 2, further characterized by
(a) said appliance comprising a fluid-driven toothbrush appliance.

7. The combination of claim 6, further characterized by
(a) said toothbrush appliance having a body of generally elongated, slim configuration to accommodate manual holding and manipulation,
(b) a brush element at one end of said appliance, and
(c) said first and second tubes being connected to the appliance at the other end thereof and being generally co-axial with the longitudinal axis of said body.

8. The combination of claim 1, further characterized by
(a) said fluid device comprising a source of fluid under pressure.

9. The combination of claim 1, further characterized by
(a) said end forming means comprising integral, open end portions of said flexible tubes, and
(b) said flange means comprising integral flanges on said open end portions.

10. The combination of claim 1, further characterized by
(a) said end forming means comprising swivel connectors affixed to the ends of said tubes.

11. The combination of claim 10, further characterized by
(a) said swivel connectors comprising sleeve-like elements having portions received on and secured to said tubes, and
(b) said flange means comprising integral flanges on said sleeve-like elements.

12. The combination of claim 1, further characterized by
(a) said first tube being received within said second tube,
(b) said first tube being formed of a material selected primarily for physical properties, and
(c) said second tube being formed of a material selected at least in part on the basis of appearance characteristics.

* * * * *